United States Patent [19] [11] Patent Number: 4,956,498
Zerpner et al. [45] Date of Patent: Sep. 11, 1990

[54] COUPLING AGENTS FOR VULCANIZABLE MIXTURES OF UNSATURATED RUBBERS AND SILICON-CONTAINING FILLERS

[75] Inventors: Dieter Zerpner; Horst G. Haag, both of Marl, Fed. Rep. of Germany

[73] Assignee: Huels Aktiengesellschaft, Marl, Fed. Rep. of Germany

[21] Appl. No.: 373,272

[22] Filed: Jun. 28, 1989

[30] Foreign Application Priority Data

Jun. 28, 1988 [DE] Fed. Rep. of Germany ....... 3821670

[51] Int. Cl.$^5$ .................. C08K 3/34; C08C 19/00; C08F 20/44
[52] U.S. Cl. .................. 524/492; 525/342; 525/331.8; 525/332.1; 525/332.8; 525/332.9; 525/333.2; 525/333.5; 525/329.1
[58] Field of Search ............... 524/571, 492; 556/428; 525/342, 331.8, 332.1, 332.8, 332.9, 333.2, 333.5

[56] References Cited
FOREIGN PATENT DOCUMENTS
191929 8/1986 European Pat. Off. .

Primary Examiner—Joseph L. Schofer
Assistant Examiner—Mark D. Sweet
Attorney, Agent, or Firm—Oblon, Spivak, McClelland, Maier & Neustadt

[57] ABSTRACT

A coupling agent for vulcanizable mixtures of rubbers and mineral fillers which is the reaction product of a 2(3)-chloroacetoxy-5-(2'-trialkoxysilyethyl)norbornane of the formula:

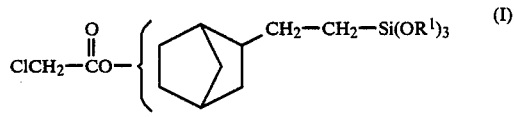

wherein $R^1$ is methyl and/or ethyl, with a thiosulfonic acid salt of the formula:

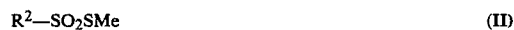

$$R^2 - SO_2SMe \qquad (II)$$

wherein $R^2$ is a (cyclo)aliphatic or aromatic hydrocarbon radical having up to 20 carbon atoms, and Me is sodium or potassium.

6 Claims, No Drawings

COUPLING AGENTS FOR VULCANIZABLE MIXTURES OF UNSATURATED RUBBERS AND SILICON-CONTAINING FILLERS

BACKGROUND OF THE INVENTION

1. Field of the Invention

The present invention relates to a technique of reinforcing olefinically unsaturated rubbers.

2. Description of the Background

The most important reinforcing fillers known to the present for olefinically unsaturated rubbers are active carbon blacks having a large surface area.

The replacement of carbon black by silicon-containing fillers of comparably large surface area is economically interesting for the preparation of pale or colored vulcanizates. Although the tear propagation strength of the vulcanizates prepared in this way is improved, all of the other rubber-technological properties are, however, significantly impaired. It is known to compensate for this shortcoming to a greater or lesser extent by adding a so-called coupling agent to the rubber. The coupling agent has the task of ensuring bonding between the hydrophilic silicon-containing filler and the hydrophobic unsaturated rubber components of the mixture. Particularly good coupling agents for this purpose have proven to be organofunctional silanes, which form siloxane bonds with the silicon-containing filler by means of reactive silicon-containing groups and which form sulfur bonds with the rubber during the vulcanization by means of sulfur-containing groups (cf. Ullmann's Encyklopadie der Technischen Chemie, Volume 21, page 498, Verlag Chemie, 4th edition).

A known coupling agent is 3-mercaptopropyltriethoxysilane. However, its odor makes it use disadvantageous. For this reason, coupling agents which overcome this disadvantage have been employed which have the formula:

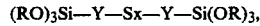

wherein R is methyl and/or ethyl, X is 2 to 6, usually about 4, and Y is a divalent saturated hydrocarbon radical having 1 to 5 carbon atoms and a linear or branched carbon chain, which is optionally interrupted by —O—, —S—, or —NH— (German Auslegeschrift No. 2,712,866), or Y is

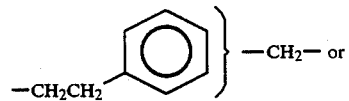

(EP-Al-O,191,929).

Since coupling agents of the last-mentioned type contain an average of four sulfur atoms, they are known as "tetrasulfanes". However, these compounds exhibit the disadvantage that they must be employed, above all, in not inconsiderable amounts with respect to highly disperse silicas in order to obtain tension values, for example, at 300% elongation, which are improved by a multiple over a comparison vulcanizate which does not contain a coupling agent. In addition, the synthesis of a "tetrasulfane" requires anhydrous $Na_2S_4$, whose preparation is not without problems because of the use of metallic sodium. A need therefore continues to exist for a coupling agent which improves upon the bonding between unsaturated rubber and added inorganic filler.

SUMMARY OF THE INVENTION

Accordingly, one object of the present invention is to provide a coupling agent for use in a vulcanizable mixture with an inorganic filler from which a vulcanizate of improved properties is prepared.

Briefly, this object and other objects of the present invention as hereinafter will become more readily apparent can be obtained by the incorporation of a coupling agent in a vulcanizable mixture is which the reaction product of a 2(3)-chloroacetoxy-5-(2'-trialkoxysilylethyl)norbornane of the formula:

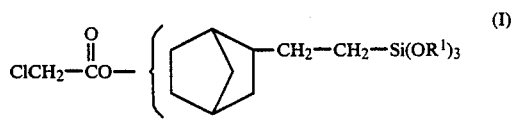

wherein $R^1$ is methyl and/or ethyl, with a thiosulfonic acid salt of the formula:

wherein $R^2$ is a (cyclo)aliphatic or aromatic hydrocarbon radical having up to 20 carbon atoms, and Me is sodium or potassium.

DETAILED DESCRIPTION OF THE PREFERRED EMBODIMENTS

The discovery of the present invention is a coupling agent which contains a combination of functional groups, not previously known, which results in a vulcanizate of very good rubber-technological properties. The coupling agent of the present invention is prepared from a compound of the formula: 2(3)-chloroacetoxy-5-(2'-trialkoxysilylethyl)norbornane of the formula:

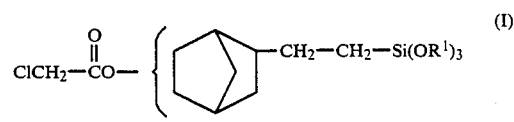

wherein $R^1$ is methyl and/or ethyl.

The coupling agent of the invention can be prepared from the commercially available material 5-vinylnorborn-2-ene in a 2- or 3-step process.

The first step of the synthesis is the selective addition of chloroacetic acid to the cyclic double bond of the 5-vinylnorborn-2-ene to form a mixture of 2(3)-chloroacetoxy-5-vinylnorbornane isomers. In the second step of the process of preparing the compound, trimethoxysilane and/or triethoxysilane is reacted with the adduct to give the ester of the formula I.

In the three-step process of preparing the compounds, the 2(3)-chloroacetoxy-5-vinylnorbornane isomer mixture prepared in the first step is reacted with trichlorosilane. The product is then reacted with an alcohol which introduces methoxy or ethoxy groups into the molecule. The reaction occurs in the presence of a tertiary amine base which removes hydrogen chloride produced in the reaction. The amine base is conveniently employed in a slight molar excess of 1:1 to 1:1.2.

In principle, other known processes for converting the trichlorosilyl group of the intermediate in the three-step process into trialkoxysilyl groups can be employed. For example, the intermediate can be reacted with appropriate orthoesters or alcoholates. In that event an amine base is not required to remove HCl.

To complete the preparation of the coupling agent, the silyl compound of formula I is reacted with a thiosulfonic acid salt of the formula:

$$R^2\text{—}SO_2SMe \qquad (II),$$

in which $R^2$ is a $C_1$–$C_{20}$ aliphatic hydrocarbon radical a $C_5$–$C_{20}$ cycloaliphatic hydrocarbon radical or a $C_6$–$C_{20}$ aromatic hydrocarbon radical, and Me is sodium or potassium. These salts are known and can be prepared, for example, by reacting the appropriate sulfonyl chloride with sodium sulfide in aqueous or alcoholic solution or by sulfurizing the appropriate sulfinic acid salt with an amine (Houbel-Weyl-Muller, Volume E11/Part 2, page 1112; Methodicum Chimicum, Volume 7, page 730, G. Thieme Verlag, Stuttgart, 1976).

To prepare the coupling agent of the present invention, the compounds of formulas I and II are reacted in a manner similar with known esterification reactions where the reactants are reacted in a solvent of methanol or ethanol (Houben-Weyl-Muller, Volume E11/Part 2, page 1118; Methodicum Chimicum, Volume 7, page 732, G. Thieme Verlag, Stuttgart, 1976). Other suitable solvents include, for example, dimethylforamide, dimethylacetamide and N-methylpyrrolidone.

The reaction is generally carried out at temperatures of from 50° to 100° C., preferably 60° to 80° C. When methanol or ethanol is used, it is advisable to carry out the reaction at the boiling points of alcohol employed.

At the end of the reaction, the solvent is removed by evaporation as much as is possible, and the product is separated from the sodium chloride or potassium chloride coproduct, by washing the product with suitable solvent, such as, for example, toluene, cyclohexane, dimethyl ether or methyl tert.-butyl ether.

A particular advantage of the coupling agent obtained in the manner described is that it need not be separated further from the rubber, but instead can be employed as a crude product which has been freed from solvents and inorganic byproducts.

Suitable rubbers from which the vulcanizate can be prepared using the coupling agent of the present invention include, for example, styrene-butadiene rubber (SBR), natural rubber (NR), polyisoprene rubber (IR), polybutadiene rubber (BR), acrylonitrilebutadiene rubber (NBR), ethylene-β-olefin-(diene) rubber [EP(D)M], butyl rubber (IIR), and polyalkenylene rubber, such as polypentenylene, polyoctenylene or polydodecenylene rubber.

Additives which can be employed in the vulcanizable mixtures include plasticizer oils which are normally used in rubber technology. Aromatic, aliphatic and naphthenic hydrocarbons are preferred. They can be added in the customary amounts. Other customary auxiliaries include the likes of zinc oxide, stearic acid, resin acids, antiageing agents and ozone-protection waxes, in the customary amounts.

The active, reinforcing filler of the vulcanizable mixture is generally comprised of at least 10, in particular at least 30% by weight of a highly disperse filler select from the group of silicas, silicates and mixtures thereof, which have been treated (coated) with the coupling agent in the presence of the rubber component, in situ, and at most 90, in particular at most 70% by weight of other active, reinforcing fillers. The coupling agent plus silica or silicate filler is equivalent to the amount of filler treated in situ.

The amount of reinforcing inorganic filler in the composition ranges from 10 to 100 parts by weight per 100 parts by weight of rubber. For other fillers the amount ranges from 30 to 90 parts by weight per 100 parts by weight of rubber.

The surface area of the filler before treatment is generally 30 to 500, in particular 35 to 300 m$^2$/g, as determined by nitrogen adsorption by the BET method. The amount of coupling agent employed generally ranges from 0.5 to 10, in particular 1 to 6% by weight, based on the untreated filler.

The coupling agent of the present invention can be handled and used in the rubber-processing industry, for example, as an internal mixture, or as a roll, expediently before the vulcanization system comprising sulfur and the customary accelerators. The crosslinking density and the vulcanization rate can be varied as usual within broad limits through the choice of the type and amount of the vulcanization accelerators and the amount of sulfur and/or sulfur donors.

Having generally described this invention, a further understanding can be obtained by reference to certain specific examples which are provided herein for purposes of illustration only and are not intended to be limiting unless otherwise specified.

Unless otherwise stated, all % data in the following examples denote percent by weight, M denotes the relative molecular weight and Mn denotes the number average relative molecular weight. The molecular weights are determined by vapor pressure osmometry. The amounts given in parts are parts by weight. HPLC is an abbreviation for high-pressure liquid chromatography.

Preparation of 2(3)-chloroacetoxy-5-vinylnorbornane

A 720 g amount of 5-vinylnorborn-2-ene (purity determined by gas chromatography at least 98%), 842 g of chloroacetic acid and 450 ml of dry xylene are heated to 140° C. under dry nitrogen in a 3-necked flask fitted with internal thermometer, stirrer and reflux condenser, the slightly exothermic reaction setting in at about 120° C. The temperature of the reaction mixture was kept at 140° C. for a further two hours, the mixture was cooled, the excess chloroacetic acid was removed by dissolution in water, and the organic phase was washed with sodium bicarbonate solution and water until neutral. After drying over calcium chloride, distillation in vacuo gave 928 g (72% of theory) of a colorless liquid ($n_D^{20}$:1.4951). The structure given (isomer mixture) was confirmed by NMR and GC analyses.

Preparation of 2(3]-chloroacetoxy-5-(2'-triethoxysilyl-ethyl)norbornane

A 429 g amount of 2(3)-chloroacetoxy-5-vinylnorbornane was warmed to 80° C. under dry nitrogen together with 0.1 ml of a solution of 200 mg of hexachloroplatinic acid in 10 ml of tetrahydrofuran in a 3-necked flask fitted with internal thermometer, stirrer, reflux condenser and dropping funnel, and 220 ml of trichlorosilane were subsequently added dropwise over the course of 30 minutes, during which the temperature of the exothermic reaction was kept at 80° C. by cooling. When addition of the trichlorosilane was complete, the reaction mixture was kept at 80° C. for a further 1.5 hours, and readily volatile components were then removed by distillation in vacuo.

The reaction product obtained, 2(3)-chloroacetoxy5-(2'-trichlorosilylethyl)norbornane of formula I with —SiCl$_{13}$ in place of —Si(OR$^{l}$)$_3$, was added via a dropping funnel under dry nitrogen to a vigorously stirred mixture of 2 liter of ethanol and 120 ml of triethylamine. During this addition, the temperature of the reaction mixture was kept at between 10° and 15° C. by cooling, while simultaneously a further 956 ml of triethylamine was added dropwise at a rate such that addition of both liquids was complete simultaneously after about 30 minutes. The mixture was subsequently stirred without cooling for a further 60 minutes, and the precipitated salt (amine hydrochloride) was removed by filtration with suction and washed twice with 800 ml of dry toluene. After the solvent had been removed by distillation on a rotary evaporator, the filtrates were mixed with 200 cm$^3$ of dry toluene, the precipitated salt was removed by filtration with suction and washed with toluene, and the filtrate was freed from toluene. 710 g (94% of theory) of a crude product ($n_D^{20}$:1.4656) were obtained. Distillation in vacuo gave 612 g (81% of theory) of a colorless liquid ($n_D^{20}$:1.4621). The structure given (isomer mixture) was confirmed by NMR and GC analyses.

Preparation of 2(3)-chloroacetoxy-5-(2'-trimethoxy-silylethyl)norbornane

The above procedure was modified by replacing the ethanol with methanol. A 598 g amount (89% of theory) of crude product ($n_D^{20}$:1.4720) was obtained. Distillation in vacuo gave 530 g (79% of theory) of a colorless liquid ($n_D^{20}$:1.4700).

Preparation of sodium benzenethiosulfonate (Method I)

A 126.6 g amount of Na$_2$S.xH$_2$O (60 to 62 percent by weight of Na$_2$S) was substantially dissolved with stirring under dry nitrogen in 2 liter of technical-grade absolute ethanol at 25° C., and 173.6 g of benzenesulfonyl chloride was added dropwise at a rate such that the reaction mixture was heated to the boiling point and a gentle reflux was maintained during the addition. The mixture was then kept at the reflux temperature for a further 30 minutes, the reaction mixture was cooled, the sodium chloride which precipitated was removed by filtration with suction and washed with ethanol, and the filtrates were evaporated to dryness in vacuo in a rotary evaporator. After drying in a vacuum drying oven (50° C., 20 mbar, desiccant KOH), the weight of the white salt was 194.0 g and contained, according to HPLC, an average of 85% of sodium benzenethiosulfonate.

(Method II)

Na$_2$S.x H$_2$O (60 to 62 percent by weight of Na$_2$S) was dried in a water separator under dry nitrogen using xylene, the xylene was decanted, and the residue, as described above, was dissolved and reacted with benzenesulfonyl chloride. After an HPLC analysis in order to determine the thiosulfonate content, the reaction mixture was employed in the next step without removing the sodium chloride produced.

(Method III)

A sodium benzenesulfinate was reacted with sulfur as described in Synthesis, 1980, page 615. The content of sodium benzenethiosulfonate in the product was at least 97%.

Other sodium thiosulfonates and potassium thiosulfonates can be obtained in the same way from the corresponding sulfonyl chlorides or metal sulfinates.

Preparation of the coupling agent of the invention

EXAMPLE 1

A 47.5 g amount (85 %; 0.206 mol, based on 100% pure product) of sodium benzenethiosulfonate was substantially dissolved in 400 ml of dry ethanol at the reflux temperature under dry nitrogen in a 3-necked flask fitted with internal thermometer, stirrer, reflux condenser and dropping funnel, and 75.7 g (0.2 mol; 97% of 2(3)-chloroacetoxy-5-(2'triethoxysilylethyl)norbornane was subsequently added dropwise over the course of 5 minutes. The reaction mixture was refluxed for a further 2 hours and cooled, and the sodium chloride which precipitated was separated and washed with ethanol. The combined filtrates were freed from ethanol under reduced pressure in a rotary evaporator, the residue was dissolved in dry diethyl ether which was removed in the same way as the ethanol.

Yield: 95.6 g of an orange, liquid reaction product $n_D^{20}$ 1.523 C/H/S/Si;

calc. % 53.49/6.98/12.40/5.43 M$_n$=516
found % 53.24/6.64/11.3 /5.62 M$_n$=680 ,

EXAMPLES 2 TO 8

The products described in Table 1 were prepared analogously to Example 1. In the reaction of 2(3)-chloroacetoxy-5-(2'-trimethoxysilylethyl)norbornane, ethanol was replaced by methanol.

Preparation of the rubber mixtures (a) Base mixture

The following components were mixed in an internal mixer, during which mixing the temperature increased to about 140° C.

|  | Parts |
| --- | --- |
| Rubber (SBR 1502) | 100 |
| Zinc oxide, active | 3 |
| Stearic acid | 2 |
| Highly disperse, precipitated silica (Surface area: 170 m$^2$/g, determined by N$_2$ adsorption by the BET method) | 50 |
| Antiageing agent (mixture of aralkylated phenols) | 1 |

| Coupling agent (see Table 2) | variable |
| --- | --- |
| Dibenzothiazyl disulfide | 1 |
| Diphenylguanidine | 2 |
| Sulfur | 2 |

A given preparation was then vulcanized in the customary manner in a press at 150° C. In order to prevent any variations in the vulcanization process greatly affecting the values to be measured on the test specimens, all the test values were obtained as shown in Table 2, after a vulcanization time of 25 minutes (about 10 minutes longer than corresponds to t$_{90}$).

TABLE 1
Preparation of the Coupling Agents of the Invention by Reaction of I with II

| | Reactants | | | | | | | Product | |
|---|---|---|---|---|---|---|---|---|---|
| | II | | I | | | | | Analytical Values | |
| Ex. | type $R^2$ | amount[a] [g] | type $R^1$ | amount[a] [g] | Yield [g] | $n_D^{20}$ | $M_n$ | C/H/S/Si | |
| 2 | ⌬— (phenyl) | 80.8 | $CH_3$ | 134.6 | 148.3 | 1.532 | 1450 / 474 | 50.25/6.17/13.0/7.09% / 50.63/6.33/13.50/5.91% | found / calc. |
| 3 | $(C_{12}H_{25})$—⌬— (b) | 75.0 | $CH_3$ | 67.3 | 124.0 | 1.518 | 1420 / 684 | 58.61/8.28/9.50/4.52% / 59.81/8.41/9.97/4.36% | found / calc. |
| 4 | $(C_{12}H_{25})$—⌬— (b) | 75.0 | $C_2H_5$ | 75.7 | 130.6 | 1.509 | 1080 / 642 | 60.06/8.43/9.02/3.98% / 61.40/8.77/9.36/4.09% | found / calc. |
| 5 | $CH_3$—⌬— | 86.6 | $CH_3$ | 134.6 | 170.1 | 1.535 | 1080 / 488 | 51.90/6.47/12.3/5.93% / 51.64/6.56/13.11/5.74% | found / calc. |
| 6 | $CH_3$—⌬— | 43.3 | $C_2H_5$ | 75.7 | 95.2 | 1.526 | 1270 / 530 | 54.13/6.89/11.7/5.34% / 54.34/7.17/12.08/5.28% | found / calc. |
| 7 | $nC_{12}H_{25}$— | 59.3 | $CH_3$ | 67.3 | 92.9 | 1.490 | 960 / 566 | 53.35/8.51/9.83/5.14% calc. / 55.12/8.83/11.31/4.95% | found |
| 8 | $nC_{12}H_{25}$— | 59.3 | $C_2H_5$ | 75.7 | 95.5 | 1.487 | 1110 / 608 | 56.59/8.88/11.2/5.08% calc. / 57.24/9.21/10.53/4.61% | found |

(a) calculated for 100% thiosulfonate
(b) prepared from MARLON ® $AS_3$ with $C_{10}$–$C_{13}$ and the following average C number distribution:
C: 10% by wt. 4–6
 11% by wt. 43–49
 12% by wt. 36–40
 13% by wt. 10–13
 14% by wt. at most 1

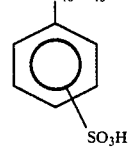

$C_{10}$–$C_{13}$ $SO_3H$

Content of 2-Phenylalkane: 15 +/− 5% by wt.

TABLE 2
Application Test Values of the Vulcanized Test Specimens

| Coupling Agent From Example | A[1] | 1 | 6 | B[2] | B[2] | 1 | 6 | 3 |
|---|---|---|---|---|---|---|---|---|
| Parts | — | 1 | 1 | 1 | 2 | 2 | 2 | 2 |
| Tensile strength (DIN 53 504) [MPa] | 11.5 | 15.7 | 18.1 | 12.8 | 13.2 | 17.7 | 18.1 | 17.5 |
| Elong. at break (DIN 53 504) [%] | 546 | 479 | 528 | 386 | 348 | 456 | 429 | 419 |
| Tension value (DIN 53 504) [MPa] | | | | | | | | |
| at 200% elongation | 2.5 | 4.1 | 4.5 | 5.2 | 6.1 | 5.6 | 6.1 | 6.1 |
| at 300% elongation | 3.9 | 7.6 | 7.7 | 8.9 | 10.8 | 10.0 | 11.0 | 11.2 |
| Tear propagation strength (internal method) according to [N/mm] Pohle | 20 | 27 | 27 | 24 | 24 | 34 | 30 | 31 |
| Shore A hardness (DIN 53 505) | 65 | 67 | 67 | 70 | 72 | 69 | 69 | 68 |
| Rebound elasticity (ISO IR 1767) [%] | 47 | 49 | 49 | 50 | 52 | 50 | 49 | 49 |
| Abrasion (DIN 53 516) [mm$^3$] | 152 | 122 | 126 | 118 | 104 | 107 | 106 | 110 |

[1] Comparison mixture A contains no coupling agent
[2] Comparison mixture B contains bis-(3-triethoxysilylpropyl)tetrasulfane which is an example of a coupling agent k in the art.

It is evident from the data presented in Table 2 that the coupling agent of the invention greatly improves all the test values in comparison to the vulcanizate of Example A which was prepared without the use of a coupling agent. Compared with the coupling agent of the prior art, corresponding to the vulcanizates of Comparative Example B1 and B2, the coupling agent of the invention results in less stiffening, since a considerably grater elongation at break is retained at comparable tension alues. The considerable increase in tensile strength, accompanied by an increased tear propagation strength, is particularly surprising.

Obviously, numerous modifications and variations of the present invention are possible in light of the above teachings. It is therefore to be understood that within the scope of the appended claims, the invention may be practiced otherwise than as specifically described herein.

We claim:

1. A vulcanizable mixture, comprising:
   (a) an unsaturated rubber;
   (b) an inorganic filler;
   (c) a coupling agent which is the reaction product of a 2(3)-chloroacetoxy-5-(2'-trialkoxysilylethyl)norbornane of the formula:

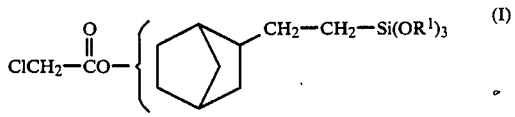

wherein $R^1$ is methyl and/or ethyl, with a thiosulfonic acid salt of the formula:

wherein $R^2$ is a (cyclo)aliphatic or aromatic hydrocarbon radical having up to 20 carbon atoms, and Me is sodium or potassium; and
   (d) rubber processing additives.

2. The mixture of claim 1, wherein said rubber is styrene-butadiene rubber, natural rubber, polyisoprene rubber, polybutadiene rubber, acrylonitrile-butadiene rubber, ethyl-$\alpha$-olefin (diene) rubber, butyl rubber, or polyalkylene rubber.

3. The mixture of claim 1, wherein the filler is a silica, silicate or mixture thereof.

4. The mixture of claim 1, wherein the surface area of the filler ranges from 30 to 500 m²/g.

5. The mixture of claim 1, wherein the amount of coupling agent employed ranges from 0.5 to 6.0% by weight, based on the inorganic filler.

6. A vulcanized rubber product obtained by vulcanization of the vulcanizable mixture of claim 1.

* * * * *